United States Patent [19]

Candau et al.

[11] Patent Number: 5,776,480
[45] Date of Patent: Jul. 7, 1998

[54] COSMETIC OR DERMATOLOGICAL COMPOSITION CONTAINING A MIXTURE OF CERAMIDES FOR MOISTURIZING THE SKIN

[75] Inventors: Didier Candau, Bievres; Carine Khayat, La Varenne; Jean-François Nadaud, Clamart; Dominique Agnus-Ancilotti, La Varenne St. Hilaire, all of France

[73] Assignee: L'Oreal, France

[21] Appl. No.: 572,673

[22] Filed: Dec. 14, 1995

[30] Foreign Application Priority Data

Dec. 14, 1994 [FR] France ................. 94 15074

[51] Int. Cl.⁶ ........................................... A61K 7/48
[52] U.S. Cl. ..................... 424/401; 514/887; 514/886; 514/847
[58] Field of Search ........................ 424/401; 514/887, 514/886, 847

[56] References Cited

U.S. PATENT DOCUMENTS 5,368,857 11/1994 Corcoran et al. .
5,401,517 3/1995 Meyers ................................ 424/401
5,476,671 12/1995 Cho ................................... 424/70.1

FOREIGN PATENT DOCUMENTS

WO-A-9001323 2/1990 WIPO .

OTHER PUBLICATIONS

Kerscher et al., "Skin Ceramides: Structure and Function," European Journal of Dermatology, 1(1):39–43 (1991).
Patent Abstracts of Japan, vol. 11, No. 115 (C–415) (2562), 1987, Patent Date: Nov. 18, 1986.

*Primary Examiner*—Thurman K. Page
*Assistant Examiner*—D. Faulkner
*Attorney, Agent, or Firm*—Finnegan, Henderson, Farabow, Garrett & Dunner, L.L.P.

[57] ABSTRACT

A cosmetic or dermatological composition containing a mixture of at least one type-III ceramide in the form of a single stereoisomer and of at least one type-V ceramide. This mixture is in particular a mixture having a melting point which is much lower than that of the type-III ceramide. This composition is intended in particular for moisturizing dry skins.

22 Claims, 1 Drawing Sheet

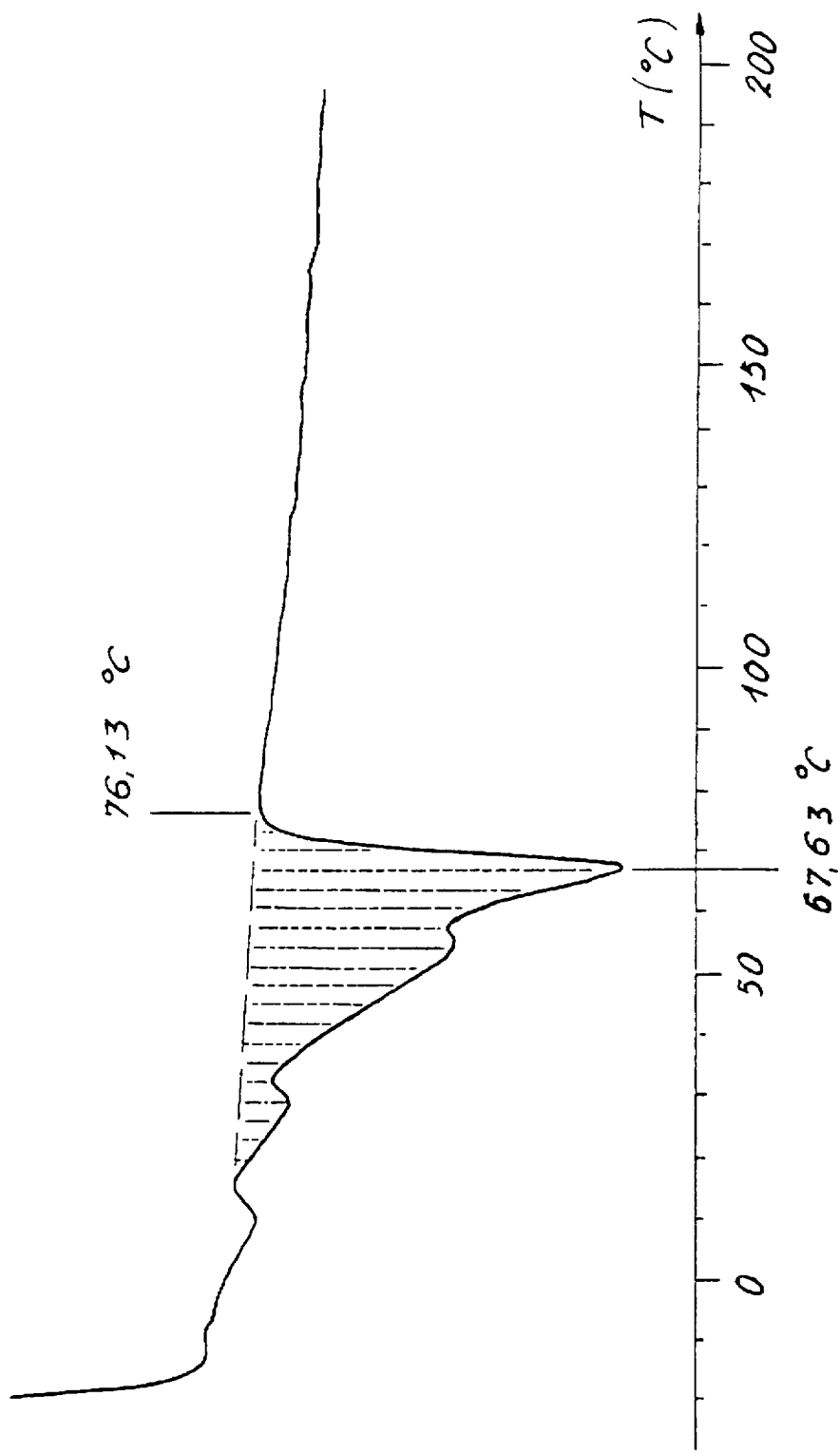

COSMETIC OR DERMATOLOGICAL COMPOSITION CONTAINING A MIXTURE OF CERAMIDES FOR MOISTURIZING THE SKIN

The invention is directed to a cosmetic or dermatological composition containing a mixture of ceramides and in particular a mixture of at least one type-III ceramide with other types of ceramides which make it possible in particular to moisturize the skin, both of the face and of the body, or indeed even of the scalp and nails. The invention is more particularly directed to a moisturizing composition of this type.

The invention is also directed to the use of this composition for moisturizing the skin, for preparing a dermatological ointment or salve for treating very dry skin, and to a process for the cosmetic treatment of the skin. The invention is also directed to a process for lowering the melting point of a type-III ceramide.

The skin of the body and more particularly that of the face is constantly subjected to environmental attack, such as from wind, cold or dust, leading to a significant water loss from the skin which must be continuously compensated for. A dehydration of the skin is reflected by a skin which is often wrinkled, harsh and rough, which has a tendency to desquamate and which has lost its elasticity. In addition, dehydration, except in the case of skin diseases, is often synonymous with aged skin. However, there is an increasing desire for one's skin to appear young and less wrinkled.

Many cosmetic or dermatological compositions which are on the market are intended for the treatment of dry skin or skin with a dry tendency. To achieve this, these compositions contain moisturizing active ingredients, such as polyols (glycerol), which unfortunately confer an often sticky feel to these compositions, thus deterring many consumers from using them. They can also contain hydroxy acids and/or their salts which have the disadvantage of stinging, irritating and warming the skin, which results in a certain degree of discomfort for the user. There also exist compositions which contain oils or other fatty substances as moisturizing active ingredients or active ingredients which prevent dehydration, resulting in compositions which often take a long time to penetrate into the skin and which leave a greasy film on the skin, which is also not much appreciated by users.

There is consequently an ongoing search to introduce into cosmetic or dermatological compositions new moisturizing active ingredients or active ingredients which prevent dehydration of the skin and seek to achieve restoration of its barrier effect to environmental attacks.

The use of ceramides or pseudoceramides as moisturizing agents and/or agents for restructuring the skin for the purpose in particular of preventing and/or controlling cutaneous aging has recently been addressed (see in particular European Patent Numbers EP-A-556,957, EP-A-587,288 and EP-A-542,549, the disclosures of which are specifically incorporated herein by reference).

Ceramides are a major component of the skin and especially in the upper layers of the epidermis, that is to say in the stratum corneum. A number of types of ceramides exist, depending on their location and their function in the epidermis. The term ceramide, taken in its strict sense, comprises solely lipids composed of the sphingosine family, such as sphinganine, 4-hydroxy-sphinganine or phytosphingosine, which are bonded to a fatty acid or fatty acid derivative via their amine functional group.

The ceramides of the stratum corneum are composed of 6 chromatographically distinct fractions having a different polarity according to the degree of unsaturation (which may be zero) or of hydroxylation of their chains, their length and their number. These ceramides are categorized according to their chemical configuration as class I, II, III, IV, V, VIa and VIb. Their chemical configuration is in particular provided in the document "Ceramides, Key Components for Skin Protection," by R. D. Petersen, Cosmetics & Toiletries, vol. 107, February 1992, p. 45–49 and the document in EJD, No. 1, vol 1, October 1991, Review article, p. 39–43, "Skin Ceramides: Structure and Function," by M. Kerscher.

The lipids of the intercorneocytic cement of the skin, and in particular the ceramides, are arranged in lamellar double layers, or lamellae, and take part in the cohesion of the stratum corneum for the purpose of keeping the barrier whole and for maintaining its protective, anti-penetration or anti-irritant role, and the like.

The most important for the barrier property is the physical state of the double layers, that is, in lamellar form.

The ceramides that are introduced into cosmetic or dermatological compositions can be extracted from the skin or alternatively synthesized. Their extraction from the skin is not always easy. In addition, it is not possible to obtain, by conventional chemical synthesis, a pure ceramide which can achieve, either hydrated or in combination with other lipids, a lamellar structure like the ceramides of the skin. Rather, a racemic mixture is always obtained, which mixture poses problems of purification, e.g., in difficulty and length of the processes.

Only type-III ceramides synthesized to date have the advantage of having the same stereoisomeric structure as the ceramides of the skin and of being pure. Due to this stereoisomerism, these ceramides can arrange themselves in lamellae, like the intracellular cement. A better compatibility with the skin and an increased effectiveness with respect to ceramides having a different structure result therefrom. This stereoisomerism results from an enzymatic manufacture of these ceramides, in which stereospecific enzymes are used.

The Inventor has therefore contemplated the introduction of type-III ceramides, obtained enzymatically, into cosmetic or dermatological compositions for the purpose of restructuring, moisturizing, and/or controlling the aging of the skin. Unfortunately, these ceramides have a high melting point, of the order of 126° C., which is incompatible with the ingredients conventionally used in the fields under consideration.

In order to provide for their dissolution in cosmetic or dermatological media, it is necessary to bring the ceramides to their melting temperature, with the consequent risk of damaging the other constituents of the composition. Moreover, this high temperature greatly complicates the manufacture of the cosmetic products (specific tooling), increasing their cost prices. In addition, with this high melting temperature, the compound is found on the skin, after application, in the crystalline state. This state is excessively rigid and cannot fill the intercorneocytic spaces of the skin.

The Inventor has consequently looked for a means of lowering the melting point of type-III ceramides in the form of a single stereoisomer.

It has surprisingly been found that the combination of a type-V ceramide with a type-III ceramide in the form of a single stereoisomer made possible the formation of a mixture, the melting temperature of which is less than that of the type-III ceramide in the form of a single stereoisomer alone.

A subject of the invention is therefore a cosmetic or dermatological composition containing a mixture of at least one type-III ceramide in the form of a single stereoisomer and at least one type-V ceramide.

A further subject of the invention is a process for lowering the melting point of at least one type-III ceramide in the form of a single stereoisomer which comprises mixing at least one type-V ceramide with a type-III ceramide.

The type-III ceramide in the form of a single stereoisomer is advantageously a ceramide obtained enzymatically.

Preferably, the mixture of ceramides is a mixture of at least one type-III ceramide in the form of a single stereoisomer, at least one type-V ceramide and at least one type-II ceramide.

It is also possible to use a mixture of ceramides containing at least one type-III ceramide in the form of a single stereoisomer, at least one type-V ceramide, at least one type-II ceramide and optionally containing at least one type-IV ceramide.

The ceramides to which the invention applies generally correspond to the following formula (I):

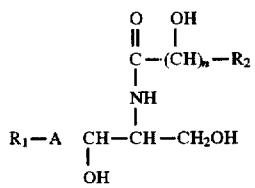

wherein A represents

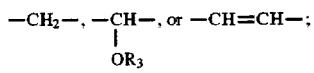

$R_1$ represents a saturated or unsaturated, linear or branched, $C_8$ to $C_{28}$, preferably $C_{10}$ to $C_{26}$, alkyl chain;

$R_2$ represents a saturated or unsaturated, linear or branched, $C_{12}$ to $C_{36}$ alkyl chain;

$R_3$ represents H or —CO—CHOH—$R_2$; and n represents 0 or 1.

The ceramides of formula I are in the form of stereoisomers or mixtures of stereoisomers. Preferably, all types of ceramides within formula I, other than type-III ceramides, are mixtures of stereoisomers.

Mention may preferably be made, as type-III ceramides which can be used in the invention, of phytosphingosine acylated by a fatty acid having from 12 to 30 carbon atoms and in particular by palmitic acid, tetracosanoic acid, linoleic acid or stearic acid. Preferably, use may be made of the ceramide III sold by the company Brocades which is N-stearoylphytosphingosine or alternatively N-{2,3-dihydroxy-1-(hydroxymethyl)hepta-decyl}octadecanamide. This product is optically active (dextrorotatory).

Mention may preferably be made, as type-V ceramides which can be used in the invention, of sphingosine acylated by a hydroxylated fatty acid having from 12 to 20 carbon atoms and in particular by 2-hydroxystearic or 2-hydroxypalmitic acid. Preferably, use is made of N-(α-hydroxypalmitoyl)dihydrosphingosine, also known under the name 2-(2'-hydroxyhexadecanoylamino)octa-decane-1,3-diol.

The ceramide II is preferably, for example, a sphinganine N-acylated by a fatty acid having from 12 to 20 carbon atoms, such as oleic, linoleic, lauric or myristic acid, such as N-oleoyldihydrosphingosine, also known as 2-oleoyl-amino-1,3-octadecanediol, and the type-IV ceramide is preferably a sphinganine N-acylated by a hydroxy acid containing 21 to 36 carbon atoms, such as N-(α-hydroxybehenoyl) dihydrosphingosine, also known as 2-(2-hydroxydocosanoylamino)octadecane-1,3-diol.

The type-V ceramide and optionally the type-II and/or type-IV ceramide are preferably present in an amount which is sufficient to lower the melting point of the mixture to a temperature preferably below 90° C., and more preferably below 85° C.

By plotting the phase diagram, it is possible for a person skilled in the art to determine the amount of each ceramide and in particular the amount of type-V ceramides which make it possible to obtain a melting point of the mixture which is preferably less than 90° C. and more preferably less than 85° C.

The lowering of the melting temperature results in an amorphous or liquid crystal product, which, after application to the skin, is more effective, particularly with respect to the barrier effect, than a crystalline product.

For a mixture of ceramides of types III and V, it is possible to use 65% by weight of ceramide of type-V and 35% by weight of ceramide of type-III, with respect to the total weight of the ceramide mixture, which makes it possible to lower the melting point from 126° C. to 82.7° C.

For a mixture of ceramides III, V and II, it is possible to use 10% by weight of ceramide III, 50% by weight of ceramide V and 40% by weight of ceramide II, with respect to the total weight of the ceramide mixture, which makes it possible to lower the melting point from 126° C. to 77.4° C., or to use 20% by weight of ceramide III, 40% by weight of ceramide V and 40% by weight of ceramide II, with respect to the total weight of the ceramide mixture, which makes it possible to lower the melting point from 126° C. to 69.8° C.

It is also possible to use a mixture of ceramides III, V, II and IV in order to lower the melting temperature to 77.8° C., with respectively, in % by weight with respect to the total weight of the ceramide mixture, 8% of ceramide III, 40% of ceramide V, 32% of ceramide II and 20% of ceramide IV.

This composition is highly suitable for moisturizing the skin. A further subject of the invention is consequently the use of the above-described composition for moisturizing the skin. However, the composition of the invention can also be used in the treatment of xeroses and in any treatment of the skin where it is necessary to protect the skin. Indeed, ceramides are known for their barrier effect.

Another subject of the invention is the use of the composition defined above for preparing a salve or an ointment intended for the therapeutic treatment of dry skins.

A final subject of the invention is a process for the cosmetic treatment of the skin, characterized in that it comprises applying a composition as defined above to the skin.

The compositions of the invention can additionally contain all the constituents conventionally used in cosmetic or dermatological compositions. In particular, they can contain a vegetable (sunflower, wheat germ), inorganic (paraffin), silicone (cyclomethicone), fluorinated (perfluoropolyether) or synthetic (purcellin oil, isopropyl myristate, cetearyl octanoate, glyceryl monostearate) oil, an aqueous phase, hydrophilic adjuvants, such as gelling agents, antioxidants (vitamin E), preservatives, opacifying agents, neutralizing agents or complexing agents, lipophilic adjuvants, such as essential oils, dyes, fatty alcohols, fatty acids, waxes or fragrances, and pigments (titanium or zinc oxides) and fillers. These adjuvants preferably represent, in total, from 0.1% to 20% of the total weight of the composition.

The composition of the invention can be provided in all the pharmaceutical dosage forms conventionally used in the fields under consideration. The composition according to the invention can thus be provided in the form of an aqueous or oily solution, of an aqueous gel, of a water-in-oil (W/O) or oil-in-water (O/W) emulsion, of a triple water/oil/water emulsion or of a dispersion of lipid vesicles (ionic or nonionic). This composition can have the appearance of a cream, of a serum, of a lotion or of a milk.

For an emulsion, use is preferably made, depending on the situation, of a W/O or O/W emulsifying system. During the use of a dispersion containing lipid vesicles, the latter preferably constitutes the emulsifying system. The amount of emulsifying system is preferably chosen from 0.1% to 10% of the total weight of the composition.

Mention may be made, as O/W emulsifier which can be used in the invention, of PEG-50 stearate and PEG-40 stearate, sold under the tradenames Myrj 53 and Myrj 52 respectively by the Company ICI; sorbitan tristearate, sold under the tradename Span 65 by the Company ICI; and sorbitan stearate, sold under the tradename Span 60 by the Company ICI.

Mention may be made, as W/O emulsifier which can be used in the invention, of the polyglyceryl-4 isostearate/ cetyldimethicone copolyol/hexyl laurate mixture, sold under the tradename Abil WE 09 by the Company Goldschmidt; and isostearyl diglyceryl succinate, sold under the tradename Imwitor 780K by the Company Hüls; or alternatively sugars.

When the composition has the form of a gel, use is preferably made of the conventional gelling agents, such as polysaccharides (xanthan gum, carob gum) and carboxyvinyl polymers.

The compositions of the invention can additionally contain active ingredients other than ceramides. These active ingredients can be hydrophilic active ingredients such as moisturizing agents, such as urea, proteins and their hydrolysates (in particular amino acids) or polyols (glycerol, sorbitol), or healing agents, such as allantoin and its derivatives. These active ingredients can also be lipophilic active ingredients, such as vitamins (vitamins A, F, B) and their derivatives. These additional active ingredients can also be hydrophilic or lipophilic screening agents for filtering visible and/or ultraviolet rays, such as octyl methoxycinnamate, or alternatively dermatological active ingredients. These active ingredients preferably represent, in total, from 0.1% to 10% of the total weight of the composition.

The description which follows is given by way of illustration and without implied limitation. The percentages in the examples are given by weight.

EXAMPLE 1

Moisturizing oil-in-water emulsion

| | |
|---|---|
| Volatile silicone 7158 from Union Carbide | 10.0 |
| Perhydrosqualene | 18.0 |
| Liquid petrolatum | 5.0 |
| Liquid lanolin | 4.0 |
| Arlacel 165 from Atlas | 6.0 |
| Tween 60 from Atlas | 2.0 |
| N-Stearoylphytosphingosine | 0.52 |
| N-(α-Hydroxypalmitoyl)dihydrosphingosine | 0.36 |
| Cetyl alcohol | 1.2 |
| Stearyl alcohol | 2.5 |
| Sodium hydroxide | 0.008 |
| Propylene glycol | 5.0 |
| Triethanolamine | 0.1 |
| Preservative | 0.3 |

| | | |
|---|---|---|
| Antioxidant | | 0.3 |
| Demineralized water | q.s. for | 100 |

The emulsion exists in the form of a white cream to be applied in the evening for repairing and moisturizing the skin. It is intended for all skins.

EXAMPLE 2

Moisturizing oil-in-water emulsion

| | | |
|---|---|---|
| Wheat germ oil | | 2.0 |
| Glyceryl monostearate | | 3.0 |
| PEG 400 | | 3.0 |
| Carbopol 941 | | 0.2 |
| Isopropyl myristate | | 1.0 |
| N-Stearoylphytosphingosine | | 0.2 |
| N-(α-Hydroxypalmitoyl)dihydrosphingosine | | 0.1 |
| Cetyl alcohol | | 3.0 |
| Stearyl alcohol | | 3.0 |
| Sodium hydroxide | | 0.008 |
| Propylene glycol | | 5.0 |
| Preservative | | 0.3 |
| Fragrance | | 0.5 |
| Demineralized water | q.s for | 100 |

This emulsion is a moisturizing white day cream which can be used for all skin types.

EXAMPLE 3

Moisturizing water-in-oil emulsion

| | | |
|---|---|---|
| Liquid petrolatum | | 10.0 |
| Protegin X from Goldschmidt | | 20.0 |
| Sunflower Oil | | 15.0 |
| Aromatic composition | | 1.0 |
| N-Stearoylphytosphingosine | | 0.02 |
| N-(α-Hydroxypalmitoyl)dihydrosphingosine | | 0.04 |
| N-Oleoyldihydrosphingosine | | 0.04 |
| Magnesium sulphate | | 0.5 |
| Glycerol | | 5.0 |
| Cetrol HE from Henkel | | 4.0 |
| Preservative | | 0.3 |
| Demineralized water | q.s. for | 100 |

This cream is more particularly intended for the night treatment of sensitive dry skins.

EXAMPLE 4

Moisturizing water-in-oil emulsion

| | |
|---|---|
| Abil WE 09 from Goldschmidt | 5.0 |
| Isopropyl myristate | 5.0 |
| Volatile silicone 7158 from Union Carbide | 8.0 |
| Aerosil R 812 from Degussa | 0.4 |
| Purcellin oil from Dragocco | 14.0 |
| Sodium chloride | 0.5 |
| Transcutol from Gattefosse | 3.0 |
| N-(α-Hydroxybehenoyl)dihydrosphingosine | 1.0 |
| N-Stearoylphytosphingosine | 0.04 |
| N-(α-Hydroxypalmitoyl)dihydrosphingosine | 0.25 |
| N-Oleoyldihydrosphingosine | 1.6 |
| Sodium hydroxide | 0.008 |
| Liquid petrolatum | 5.0 |

7
-continued

| Preservative | | 0.3 |
|---|---|---|
| Demineralized water | q.s. for | 100 |

This cream is more particularly intended for the night treatment of dry skins.

EXAMPLE 5

Aqueous/alcoholic gel

| Carbopol 940 | | 0.9 |
|---|---|---|
| N-Stearoylphytosphingosine | | 0.2 |
| N-(α-Hydroxypalmitoyl)dihydrosphingosine | | 0.1 |
| Ethyl alcohol | | 20.0 |
| Triethanolamine | | 0.3 |
| Propylene glycol | | 5.0 |
| Transcutol | | 5.0 |
| Preservative | | 0.3 |
| Fragrance | | 0.3 |
| Demineralized water | q.s. for | 100 |

This gel is intended for moisturizing and restructuring dry skins.

EXAMPLE 6

Emulsified oil-in-water gel

| Carbopol 940 | | 0.6 |
|---|---|---|
| Volatile silicone 7158 from Union Carbide | | 3.0 |
| Purcellin Oil from Dragocco | | 7.0 |
| N-Stearoylphytosphingosine | | 0.06 |
| N-(α-Hydroxypalmitoyl)dihydrosphingosine | | 0.04 |
| Ethyl alcohol | | 10.0 |
| Triethanolamine | | 0.2 |
| Tefosse 63 from Gattefosse | | 3.0 |
| Cetiol HE | | 2.0 |
| Caffeine | | 1.0 |
| Preservative | | 0.3 |
| Fragrance | | 0.4 |
| Demineralized water | q.s. for | 100 |

This gel is intended for moisturizing the body of any type of skin.

EXAMPLE 7

Aqueous gel

| Carbopol 940 | 0.6 |
|---|---|
| Transcutol | 5.0 |
| Triethanolamine | 0.3 |
| Preservative | 0.3 |
| Propylene glycol | 3.0 |
| Sodium hydroxide | 0.007 |
| N-(α-Hydroxybehenoyl)dihydrosphingosine | 0.03 |
| N-Stearoylphytosphingosine | 0.05 |
| N-(α-Hydroxypalmitoyl)dihydrosphingosine | 0.02 |

This gel is intended for moisturizing the body of sensitive skins.

EXAMPLE 8

Cream containing non-ionic liposomes

| Carbopol 940 | | 0.2 |
|---|---|---|
| Transcutol | | 3.0 |
| Triethanolamine | | 0.2 |
| Preservative | | 0.3 |
| Polyglyceryl-3 cetyl ether | | 3.8 |
| β-Sitosterol | | 3.8 |
| Dicetyl phosphate | | 0.4 |
| Sodium hydroxide | | 0.007 |
| N-Oleoyldihydrosphingosine | | 0.2 |
| N-Stearoylphytosphingosine | | 0.1 |
| Sunflower oil | | 35.0 |
| N-(α-Hydroxypalmitoyl)dihydrosphingosine | | 0.25 |
| Fragrance | | 0.6 |
| Demineralized water | q.s. for | 100 |

This gel is intended for moisturizing and restructuring dry skins, in particular during the night.

The mixtures of ceramides given in the examples are all mixtures having a lower melting point than those of the ceramides taken in isolation which form part of the mixture. In other words, the melting point of the type-III ceramides is lowered, which also results in the ultimate mixture having a lower melting point.

By way of example, the appended figure gives, for the 20% by weight of type-III ceramide, 40% by weight of type-V ceramide and 40% by weight of type-II ceramide mixture, a differential scanning calorimetry (DSC) curve. This curve gives the temperature difference between a reference cell (empty) and a measurement cell containing the mixture of ceramides as a function of the temperature of the oven containing these measurement and reference cells, given in °C. The temperature was raised at the rate of 10° C./min. The melting spike of the mixture corresponds to a temperature of 67.63° C.

What is claimed is:

1. A cosmetic or dermatological composition comprising a mixture of at least one class-III ceramide in the form of a single stereoisomer and at least one class-V ceramide, wherein any ceramides present in said mixture, other than class-III ceramides, may be present in the form of a mixture of stereoisomers.

2. A composition according to claim 1, wherein said ceramide mixture is a mixture of at least one class-III ceramide in the form of a single stereoisomer, at least one class-V ceramide, and at least one class-II ceramide.

3. A composition according to claim 1, wherein said ceramides are present in an amount which is sufficient to obtain a melting point of said mixture which is lower than 90° C.

4. A composition according to claim 3, wherein said ceramides are present in an amount which is sufficient to obtain a melting point of said mixture which is lower than 85° C.

5. A composition according to claim 1, wherein said ceramides have the formula (I):

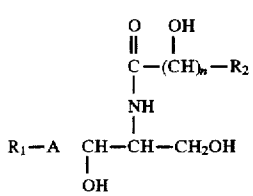

wherein A represents

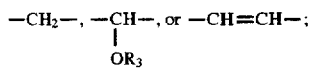

$R_1$ represents a saturated or unsaturated, linear or branched, $C_8$ to $C_{28}$ alkyl chain;

$R_2$ represents a saturated or unsaturated, linear or branched, $C_{12}$ to $C_{36}$ alkyl chain;

$R_3$ represents H or —CO—CHOH—$R_2$; and n represents 0 or 1.

6. A composition according to claim 1, wherein said ceramide mixture comprises 20% by weight of class-III ceramide, 40% by weight of class-V ceramide and further comprising 40% by weight of class-II ceramide, with respect to the total weight of the ceramide mixture.

7. A composition according to claim 2, wherein said at least one class-II ceramide is N-oleoyldihydrosphingosine.

8. A composition according to claim 1, wherein said at least one class-V ceramide is N-(α-hydroxypalmitoyl) dihydrophingosine.

9. A composition according to claim 1, wherein said at least one class-III ceramide is N-stearoylphytosphingosine.

10. A method for moisturizing the skin which comprises applying to the skin a cosmetic or dermatological composition comprising a mixture of at least one class-III ceramide in the form of a single stereoisomer and at least one class-V ceramide, wherein any ceramides present in said mixture, other than class-III ceramides, may be present in the form of a mixture of stereoisomers.

11. A method for preparing a salve or an ointment for the therapeutic treatment of dry skin which comprises combining a cosmetic or dermatological composition comprising a mixture of at least one class-III ceramide in the form of a single stereoisomer and at least one class-V ceramide, wherein any ceramides present in said ceramide mixture, other than class-III ceramides, may be present in the form of a mixture of stereoisomers, and a therapeutically acceptable carrier.

12. A method for the cosmetic treatment of skin which comprises applying to the skin a cosmetic or dermatological composition comprising a mixture of at least one class-III ceramide in the form of a single stereoisomer and at least one class-V ceramide, wherein any ceramides present in said mixture, other than class-III ceramides, may be present in the form of a mixture of stereoisomers.

13. A method for lowering the melting point of at least one class-III ceramide in the form of a single stereoisomer which comprises mixing at least one class-V ceramide with said at least one class-III ceramide, wherein any ceramides present in said mixture, other than class-III ceramides, may be present in the form of a mixture of stereoisomers.

14. A method according to claim 13, wherein said ceramides, other than said class-III ceramides, are present in an amount which is sufficient to lower the melting point of said mixture to a temperature of less than 90° C.

15. A method according to claim 14, wherein said ceramides, other than said class-III ceramides, are present in an amount which is sufficient to lower the melting point of said mixture to a temperature of less than 85° C.

16. A cosmetic or dermatological composition comprising a mixture of at least one class-III ceramide in the form of a single stereoisomer and at least one class-V ceramide, wherein any ceramides present in said mixture, other than class-III ceramides, may be present in the form of a mixture of stereoisomers, the melting point of said mixture being lower than the melting point of said at least one class-III ceramide in the form of a single stereoisomer.

17. A composition according to claim 16, wherein said ceramide mixture is a mixture of at least one class-III ceramide in the form of a single stereoisomer, at least one class-V ceramide and further comprising at least one class-II ceramide.

18. A composition according to claim 16, wherein said ceramides, other than said class-III ceramides, are present in an amount which is sufficient to obtain a melting point of said mixture which is lower than 90° C.

19. A composition according to claim 18, wherein said ceramides, other than said class-III ceramides, are present in an amount which is sufficient to obtain a melting point of said mixture which is lower than 85° C.

20. A method for moisturizing the skin which comprises applying to the skin a cosmetic or dermatological composition comprising a mixture of at least one class-III ceramide in the form of a single stereoisomer and at least one class-V ceramide, wherein any ceramides present in said mixture, other than class-III ceramides, may be present in the form of a mixture of stereoisomers, the melting point of said mixture being lower than the melting point of said at least one class-III ceramide in the form of a single stereoisomer.

21. A composition according to claim 1, which further comprises at least one class-II ceramide and at least one class-IV ceramide.

22. A composition according to claim 5, wherein $R_1$ represents a saturated or unsaturated, linear or branched, $C_{10}$ to $C_{26}$ alkyl chain.

* * * * *